(12) United States Patent
Mecher (10) Patent No.: US 9,827,081 B2
(45) Date of Patent: Nov. 28, 2017

(54) LIGHT-CURING DEVICE (75) Inventor: Erwin Mecher, Munich (DE)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 686 days.

(21) Appl. No.: 12/738,114

(22) PCT Filed: Oct. 10, 2008

(86) PCT No.: PCT/US2008/079443
§ 371 (c)(1),
(2), (4) Date: Jun. 29, 2010

(87) PCT Pub. No.: WO2009/052016
PCT Pub. Date: Apr. 23, 2009

(65) Prior Publication Data
US 2010/0273123 A1 Oct. 28, 2010

(30) Foreign Application Priority Data
Oct. 16, 2007 (GB) .................................. 0720165.0

(51) Int. Cl.
*A61C 1/00* (2006.01)
*A61C 13/15* (2006.01)

(52) U.S. Cl.
CPC .................................. *A61C 19/004* (2013.01)

(58) Field of Classification Search
CPC ... A61C 19/004; A61B 1/0661; A61B 1/0684; A61B 1/07; A61B 1/00165; A61B 3/06; A61B 3/063; A61B 5/0017; A61B 5/0059; A61B 5/0261; A61B 5/15138; A61B 2017/00057; A61B 2017/12072; A61B 2018/1807; A61B 2090/373

USPC .......... 433/29; 250/504 H, 504 R, 205, 239, 250/226, 229, 578.1, 492.3; 362/205, 239
See application file for complete search history.

(56) References Cited

U.S. PATENT DOCUMENTS

| | | | | |
|---|---|---|---|---|
| 4,385,344 A * | 5/1983 | Gonser | ........................ | 362/573 |
| 4,450,139 A * | 5/1984 | Bussiere et al. | ........... | 422/186.3 |
| 5,634,711 A * | 6/1997 | Kennedy et al. | ............. | 362/119 |
| 5,912,470 A * | 6/1999 | Eibofner | ................. | B29C 35/08 |
| | | | | 250/492.1 |
| 5,922,605 A * | 7/1999 | Feurstein et al. | ............... | 436/55 |
| 6,008,264 A * | 12/1999 | Ostler et al. | ....................... | 522/4 |
| 6,103,203 A * | 8/2000 | Fischer | ........................ | 422/186 |
| 6,309,216 B1* | 10/2001 | Parker | ............... | 433/29 |
| 6,318,996 B1 | 11/2001 | Melikechi | | |
| 6,382,967 B1* | 5/2002 | Rohner et al. | .................. | 433/29 |
| 6,384,099 B1* | 5/2002 | Ostler et al. | ....................... | 522/4 |
| 6,468,077 B1 | 10/2002 | Melikechi | | |

(Continued)

FOREIGN PATENT DOCUMENTS

| EP | 0 827 723 | 3/1998 |
|---|---|---|
| EP | 1 062 917 | 12/2000 |

(Continued)

*Primary Examiner* — Cris L Rodriguez
*Assistant Examiner* — Mirayda A Aponte (57) ABSTRACT

A light-emitting device (1) for curing dental materials. The device comprises an activator (10) and a light output (4) and is adapted to operate the light output at a first or a second operating mode dependent on the presence of a second user input within a monitoring time period after a first user input. The device allows for convenient operation by a user and helps in reliably curing dental materials.

19 Claims, 4 Drawing Sheets (56) References Cited

U.S. PATENT DOCUMENTS

| | | | |
|---|---|---|---|
| 6,482,004 B1 * | 11/2002 | Senn et al. | 433/29 |
| 6,485,301 B1 * | 11/2002 | Gemunder et al. | 433/29 |
| 6,511,317 B2 | 1/2003 | Melikechi | |
| 6,602,074 B1 * | 8/2003 | Suh et al. | 433/228.1 |
| 6,755,647 B2 | 6/2004 | Melikechi | |
| 6,918,762 B2 * | 7/2005 | Gill et al. | 433/29 |
| 7,086,862 B2 * | 8/2006 | Craig | 433/215 |
| 7,321,004 B2 | 1/2008 | Melikechi | |
| 7,407,616 B2 | 8/2008 | Melikechi | |
| 2006/0252005 A1 * | 11/2006 | Feinbloom et al. | 433/29 |
| 2007/0184402 A1 * | 8/2007 | Boutoussov et al. | 433/29 |

FOREIGN PATENT DOCUMENTS

| | | | |
|---|---|---|---|
| WO | WO 00/67660 | 11/2000 | |
| WO | WO 0067660 A1 * | 11/2000 | |
| WO | WO 2009/052016 | 4/2009 | |
| WO | WO 2009052016 A1 * | 4/2009 | A61C 19/00 |

* cited by examiner

LIGHT-CURING DEVICE

CROSS REFERENCE TO RELATED APPLICATIONS

This application is a national stage filing under 35 U.S.C. 371 of PCT/US2008/079443, filed Oct. 10, 2008, which claims priority to Great Britain Application No. 0720165.0, filed Oct. 16, 2007, the disclosure of which are incorporated by reference in their entirety herein.

The invention relates to a light-emitting device for curing dental material, which can be operated at a first or a second operating mode. The selection of the operating mode depends on the presence of a second user input within a certain time period after a first user input.

BACKGROUND OF THE INVENTION

Light curable materials are widely used in dentistry for the restoration of teeth. Such materials typically can be made to provide optical characteristics that resemble those of natural teeth, which makes those materials a favored alternative to unpleasant looking amalgam materials, for example.

Light-curable materials often include a polymerizable matrix material and filler materials including colorants, and may initially be generally soft or flowable so that they can be applied in a desired location and shape. For example, for restoration of a tooth the dental material may be filled into a tooth cavity and shaped so that the restored tooth resembles a natural tooth. Once the desired shape has been formed, the material may be cured by exposing it to light of a desired wavelength. The light typically activates photoinitiators in the dental material that cause the matrix material to polymerize.

The use of dental materials that are curable by blue light of a wavelength of between about 450 and 500 nm has become common in dentistry. Accordingly, light-emitting devices used for curing such dental materials typically emit light at such wavelengths. Such light-emitting device, for example, is available from 3M ESPE, Germany, under the trade designation Elipar™ Freelight 2 LED Curing Light.

Typically devices of the prior art have a time cut-off function that switches off the light after a certain period of time. Such devices also typically provide the possibility to set the cut-off time to certain values. However, it is still desirable to provide a device that allows easy adjustment of variables for appropriately curing dental materials in different situations. For example, over-hardening the material due to exposure to light at high intensity or for too long a duration should be avoided.

SUMMARY OF THE INVENTION

A first aspect of the invention is related to a light-emitting device for curing dental materials. The light-emitting device comprises an activator and a light output that is preferably adapted to emit light of a wavelength useful for curing a dental material. The device is further adapted to operate the light output in a first or a second operating mode dependent on the presence of a second user input within a monitoring time period after a first user input.

The monitoring time period is preferably started by the first user input. The light-emitting device preferably allows a user to activate the device to operate the light output at a first or a second operating mode by actuating only one activator.

In a preferred embodiment of the invention the light-emitting device is preferably adapted to detect the user input to the activator. In particular, the same activator is preferably adapted to detect the first and the second user input. The first user input may be the inverse, reverse, or opposite of the second user input. In particular the first user input may be a push on the activator, and the second user input may be a release of the activator.

In another embodiment of the invention the presence of a second user input within the monitoring time period activates the light output in the first operating mode, and the absence of a second user input within the monitoring time period activates the light output in the second operating mode. Inversely, it is also possible that the presence of a second user input within the monitoring time period activates the light output in the second operating mode, and the absence of a second user input within the monitoring time period activates the light output in the first operating mode.

The first and the second operating modes may involve operating the light output at at least one of different operating time periods, different light intensities and different wavelengths. Such different operating modes may, for example, be used to cure different dental materials requiring exposure to light for different time periods, at different light intensities and/or different wavelengths for curing. Preferably the light output is adapted to emit light at a wavelength of between 400 nm and 500 nm.

In another embodiment of the invention in the first operating mode the light output is activated for a first operating time period, and in the second operating mode the light output is activated for a second operating time period. The first operating time period is preferably longer than the second operating time period. Preferably the light output is activated upon the start of the first and/or second operating time periods, deactivated upon the end of the first and/or second operating time periods, and activated (preferably continuously activated) in between.

In an embodiment the first operating time period is pre-selectable by a user. The first operating time period may be pre-selectable from one of about 5, about 10, about 15, and about 20 seconds. Alternatively the first operating time period may be pre-selectable from a continuous time range, for example from between 0 seconds to 180 seconds.

In a preferred embodiment the light-emitting device of the invention comprises a second activator allowing for pre-selection of the first operating time period. The first operating time period may, for example, be pre-selectable through a push or rotary button. The second operating time period may be a fixed or predetermined time period. Preferably the second operating time period is between 0.1 seconds and 5 seconds.

The light-emitting device may be adapted to switch into a non-operative mode in response to a third user input during the period in which the device is operating in the first or the second operating mode. In the non-operative mode the light output may not emit light.

In a further embodiment of the invention the light-emitting device comprises a controller adapted to interpret the presence or the absence of the second user input within the monitoring time period to control the light output according to the first or the second operating mode. Preferably, the activator and the controller are electrically connected. Thus, the activator may detect the first and second user inputs and transmit corresponding signals to the controller. The controller may use such signal to control the light output according to the first or the second operating mode. The controller may be user programmable. For example the controller may at least enable a user to determine, or adjust, the monitoring time period. For programming the controller may comprise a communication interface connectable to a programming device, for example a personal computer equipped with suitable software.

The programming device may enable a user to determine certain operating parameters of the device, like the monitoring time period, the second operating time period, and/or alternative selection times for the operating time period, for example. The light emitting device may therefore comprise a communication interface, in particular one or more of an USB interface, RS-232 interface, Ethernet LAN interface, or generally a wireless communication interface, like a Bluetooth, or other radio frequency interface, or an optical interface, for example an infrared interface.

In another embodiment the light-emitting device comprises an indicator adapted to indicate information about the operating mode at which the device is operating. The light-emitting device may comprise a user interface for indicating such information, for example an audio (beeper, speaker), visual (binary lights, display) or tactile interface (vibration indicator). The information about the operating mode is preferably indicated by at least one sound or one or more acoustic signals, for example beeps.

A second aspect of the invention is related to a use of a controller in combination with a light-emitting device, wherein:

the light-emitting device includes an activator and a light output; and the controller is adapted to use (or to interpret) the presence or the absence of the second user input on the activator within a monitoring time period for controlling the operation of the light output according to a first or a second operating mode.

Preferably the controller is used in combination with a light-emitting device of the invention. The controller may comprise a non-volatile memory for holding a program providing for operating the light output at a first or a second operating mode dependent on an actuating time period related to a first and a second user input to the activator. Such non-volatile memory may be an EEPROM (Electrically Erasable Programmable Read Only Memory) or FRAM (Ferro-electric Random Access Memory), for example. The controller may be programmable, for example by rewriting at least certain designated parts of the memory.

A third aspect of the invention is related to a method of curing a dental material. The method preferably involves using a light-emitting device that can be operated in a first and a second operating mode. Further the method comprises the steps of:

activating the device in the second operating mode by:
providing a first user input on the activator, and
withholding a second user input suitable to activate the device in a first operating mode for the monitoring time period;
exposing the dental material to light with the device operating in the second operating mode;
wherein in the first operating mode the light output is activated for a first operating time period and in the second operating mode the light output is activated for a second operating time period that is shorter than the first time period.

The method according to the third aspect may also comprise the steps of:
providing a light-emitting device having an activator and a light output;
activating the device in a first operating mode in which the light output is activated for a first operating time period by:
providing a first user input on the activator, and
providing a second user input on the activator within a monitoring time period;
exposing the dental material to light with the device operating in the first operating mode;
activating the device in a second operating mode in which the light output is activated for a second operating time period by:
providing a first user input on the activator, and
withholding a second user input suitable to activate the device in a first operating mode for the monitoring time period;
exposing the dental material to light with the device operating in the second operating mode;
wherein the first operating time period is longer than the second operating time period.

Preferably exposing the dental material to light for a first and/or second operating time period causes the dental material to cure. The first time period is preferably between 5 seconds and 20 seconds. And the second operating time period is between 0.1 seconds and 5 seconds.

A fourth aspect of the invention is directed to a computer program for a light-emitting device. The computer program is adapted to receive input signals indicative of user inputs on an activator of the device, and to transmit output signals. The output signals are appropriate to operate a light output of the device at a first or a second operating mode dependent on a presence of a second user input within a monitoring time period after a first user input. The computer program may be retrofittable on a light-emitting device, for example on one that is already on the market. The computer program may, for example, be obtainable independently from the light-emitting device. The light-emitting device may allow for the computer program to be uploaded on the device, in particular the light-emitting device may be prepared to receive such computer program. The computer program may be installed on the light-emitting device by a user, for example by use of one or more of the interfaces mentioned above, for example via the wireless interface. The computer program may comprise a core part adapted to operate a light output of the device at a first or a second operating mode dependent on an actuating time period related to a first and a second user input to an activator of the device. The computer program may further comprise supplementary parts that are pre-configured to provide one or more of:
different operating modes,
different operating time periods,
different actuating time periods,
different light wavelengths, and
different light intensities.

The computer program may be software-based (for example, downloadable to the device), or firmware-based (for example, provided together with hardware). The computer program may also include a patch for updating the software or firmware. Further, the computer program may be user-adjustable, for example with regards to the first and/or second operating time periods, and the monitoring time period.

A fifth aspect of the invention is related to a kit, comprising a device of the invention and a computer program of the invention. The kit may further comprise the computer program on a data carrier, for example a transponder which is adapted to cooperate with a wireless interface of the device.

The invention preferably provides for convenient operation of the light-emitting device. In particular the possibility to actuate only one activator to activate the light-emitting device in a first or a second operating mode may allow for blind operation of the device. The invention may be advantageous in that it allows to be precisely guided during operation because the operating modes may be changed by operating one activator only, so that a user does not have to largely change hand position. Further, the light-emitting device of the invention is relatively easy to manufacture and may save manufacturing costs. In particular the number of activators may be reduced. The invention may also be advantageously because it may be retrofitted with existing light devices or offered as add-ons for new light-emitting devices.

DETAILED DESCRIPTION OF THE DRAWINGS

Figure 1:
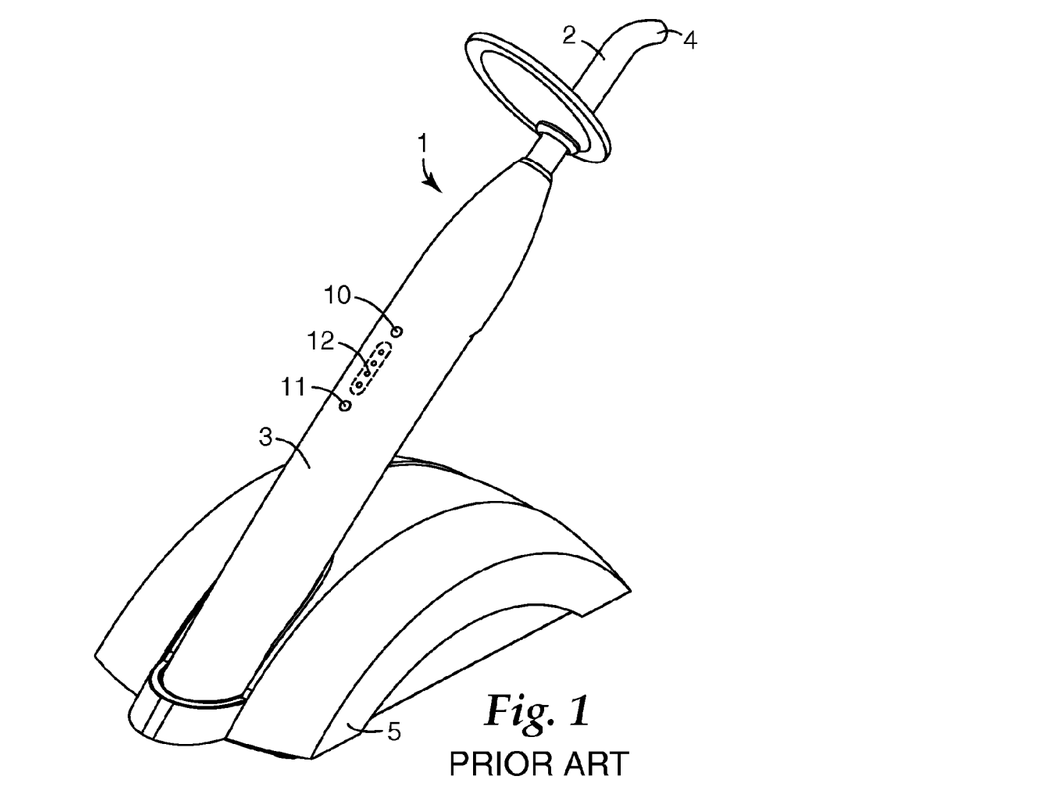
FIG. 1 is a perspective view of a light device as it may be used with the present invention.

FIG. 1 shows an exemplary light-emitting device 1 having a body 3, and a light guide 2 with a light output 4. The light-emitting device 1 is shown with a base 5 from which it is separable for use, for example, in curing a dental material. In this example, the device 1 is battery powered and therefore separable without the need of a permanent wired connection to the base 5. The exemplary light-emitting device 1 further has two buttons, an on/off button 10 and a selector button 11. The selector button 11 is typically used to pre-select a time period for which the device operates as soon as it is switched on. Therefore the device 1 can be used with different dental materials and for different applications, for example for curing layers of dental materials having different thicknesses. The on/off button 10 is typically used to switch on the device so that it operates for the time-period pre-selected by the user, and automatically switches off after. However, the device may also be switched off by pushing the on/off button at any time before the pre-selected time period has lapsed. In the device 1 shown in FIG. 1 the selector button 11 typically allows the user to pre-select between different default time periods. For example, each push on the selector button 11 may increase the operating time period by a certain time unit. Upon reaching an available maximum a further push on the selector button 11 resets the time period to a minimum again. Thus, a user can pre-select a certain time period (indicated on the device by LEDs 12) by pushing the button as often as required.

In practice the user, typically a dentist, dispenses a dental material to a desired place, for example to a tooth in a patient's mouth. The dentist then normally pre-selects the operating time period according to the dental material used and dependent on the application characteristics of the material, and presses the selector 11 accordingly. For example, the dentist may use different operating time periods for curing filling materials than for curing coatings. Other factors are typically also considered by the dentist such as material thicknesses, or the location of the material (deep in a cavity or at a tooth surface, for example). For curing the dental material the dentist typically positions the light output 4 of the device 1 close to the dental material and activates the device 1 by the activator 10. Accordingly the device emits light through the light output 4 for the pre-selected operating time period. This normally causes the dental material to cure at a rate generally correlated to the operating time period and the intensity of the light incident on the material.

The device of the invention may mechanically generally correspond to the device as shown in FIG. 1. In particular, the device may have a selector button and an on/off switch as mentioned. However, instead of buttons, as used in the example, other sensors (optical or capacitive sensors), switches (push buttons, rocking switches, slide switches), or input devices (touch panels, acoustic sensors) may be used. Therefore in the following it is more generally referred to a "selector" and an "activator". The selector generally allows a user to select between different functions or operating modes of the device, and the activator generally enables the user to switch the device on.

The device of the invention can operate at a first operating mode. The first operating mode is preferably provided with different functions that may be pre-selectable by use of the selector. Such different functions may be, for example, different operating time periods as described. However, the device of the invention also preferably allows a user, besides using the first operating mode, to select at least one alternative or second operating mode. The first and second operating modes may be distinguishable, and are preferably selectable dependent on the way the activator is used. Therefore the activator may be used to activate the device to operate at the first operating mode, or to activate the device to operate at the second operating mode. Thus, the activator is multi-functional and allows the device to be switched on and further to select between at least two different operating modes.

Figure 2:
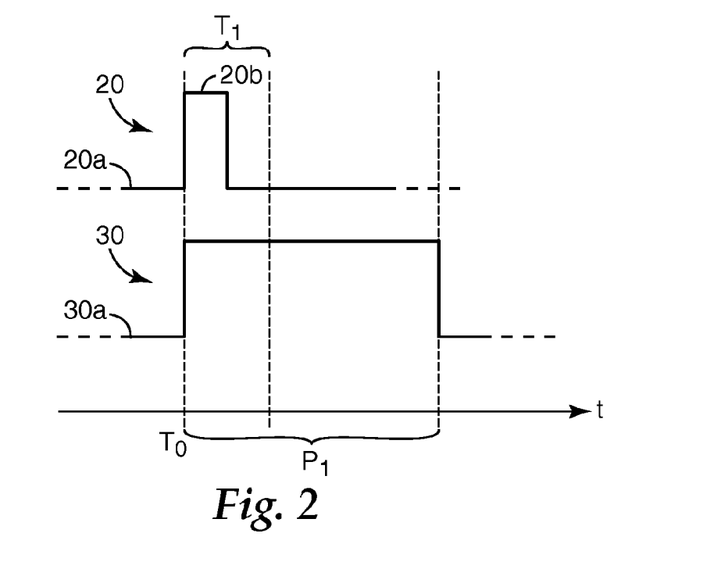
FIG. 2 is a diagram showing a first operating mode of the device according to an embodiment of the invention.
Figure 3:
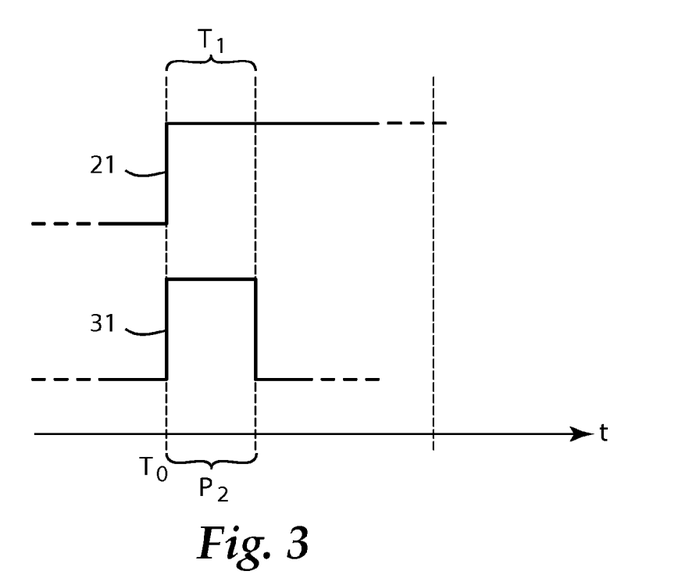
FIG. 3 is a diagram showing a second operating mode of the device according to an embodiment of the invention.

FIGS. 2 and 3 show diagrams visualizing two different operating modes as they may be activated in response to actuating the activator In FIG. 2 a curve 20 is shown which represents the actuation of the activator over time. In the initial state (curve section 20a) the activator is not actuated. At this stage the device is switched off which, and therefore does not operate so that this is not an operating mode in terms of the invention. At the time $T_0$ the activator is actuated due to a first user input and remains activated for a certain actuation time period (curve section 20b). In response to a second user input the activator is reset to its non-actuated state.

For example, if a button is used as an activator the button may close an electric circuit when it is pushed, and the electric circuit may be otherwise open. The first user input may, for example, be a push on the button which closes the electric circuit, and the second user input may be a release of the button which opens the circuit again. The status of the electric circuit may be monitored to detect a user input. The detected user inputs may be used or interpreted by a controller of the device, and the controller may control the light output, for example, depending on the presence of a second user input within a certain time period after the first user input.

In the example, a second user input is detected before the monitoring time period $T_1$ ends which triggers the light device of the invention to operate in the first operating mode. The first operating mode is represented by curve 30 of FIG. 2. The first operating mode in this example turns on the light output for a pre-selected operating time period $P_1$. For example a light output of the device (one similar to the light output 4 of FIG. 1, for example) may be initially deactivated (curve section 30a). The light output at the time $T_0$ may be activated in response to the actuation of the activator (curve 20) and may remain activated for the pre-selected operating time period $P_1$ after which it is deactivated again. The pre-selected operating time period $P_1$ may be pre-selected from different available time periods by use of the selector.

For better clarity the changeovers between low and high levels of the curves have been illustrated as vertical lines. However, in practice the changeovers may exhibit a time constant and therefore may correspond to curves that are inclined relative to the vertical.

Overall FIG. 2 visualizes an operation of the device for activating the first operating mode. A user may know similar operation principles from other light-emitting devices in which pushing and shortly thereafter releasing a button activates the device in an operating mode for which a certain operating time has been pre-selected. This may be advantageous in that the operation of the device of the invention is compatible with devices of the prior art so that a user may not require a specific training FIG. 3 shows an operation of the device for activating the second operating mode. In contrast to the situation in FIG. 2 the activator is actuated for a longer period of time. For example the second operating mode may be activated by pushing a button and holding it down for a certain period of time. In the example, the second operating mode is activated as soon as the time period between the first user input (pushing the button) and the second user input (releasing the button again) is equal or exceeds the monitoring time period $T_1$.

Figure 4:
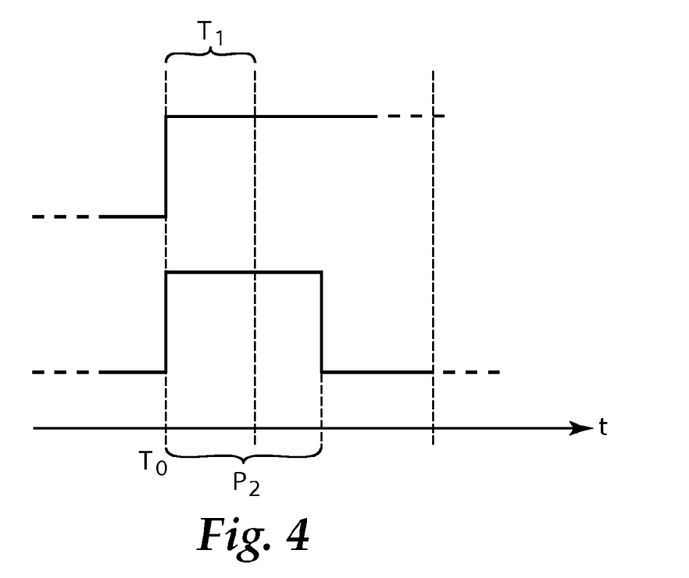
FIG. 4 is a diagram showing an alternative second operating mode of the device according to an embodiment of the invention.

In response, as represented by curve 31 of FIG. 3, the light-emitting device of the invention operates in the second operating mode. The second operating mode is independent from the first operating mode. For example, the light output may be activated at the time $T_0$ generally synchronously with the first user input (curve 21) and may remain activated for an alternative operating time period $P_2$. The alternative operating time period $P_2$ may be a default time period pre-determined in the device. However such default time period may be user programmable, for example by setting up the device using a computer program and a user interface such as a computer. The alternative operating time period $P_2$ may, for example correspond to the monitoring time period $T_1$ of FIG. 3, but as shown in FIG. 4, $P_2$ may also be different from the monitoring time period $T_1$. In particular, the operating time period $P_2$ may be shorter than the operating time period $P_1$ of the first operating mode. For example, in the second operating mode the device may activate the light output for only a short period of time. Therefore, the user can generate a flash of light of a defined time period by a single push without the need to press and release the button for only the duration of the flash.

The following table specifies exemplary time periods as they may be applicable with the present invention.

| Monitoring time period $T_1$ (seconds) | First operating mode (pre-selected operating time period) $P_1$ (seconds) | Second operating mode (alternative operating time period) $P_2$ (seconds) |
| --- | --- | --- |
| 1 | 5/10/15/20 | 1 |
| 1 | 5/10/15/20 | 2 |
| 2 | 5/10/15/20 | 2 |
| 1 | 3/6/10/20 | 1 |
| 1 | 3/6/10/20 | 2 |
| 2 | 3/6/10/20 | 2 |

Although it would be possible to provide the device with two or more buttons for the different operating modes, it is an advantage that the user does not need to change his hand or finger position during operating the device. In particular, this is advantageous because the decision to use the pre-selected operating mode or the second operating mode may be taken only when the device already has been activated. For example, a dentist could push the button for activating the light output and while observing the curing progress (for example by probing with an instrument) hold the button down for activating a shorter operating time period, or release the button for activating a longer operating time period. Dentists who typically use the light-emitting device in one hand and an instrument for shaping the material in the other hand may appreciate such convenient handling. This is because the dentist does not need to reposition his hand or finger while positioning the light-emitting device relative to the dental material. Thus he may precisely guide the device while concurrently selecting different operating modes. This may be especially advantageous for generating flashes of light of relatively short duration. Another advantage of having one instead of two or more buttons is that the user can focus on shaping the material without the need to look at the device to find the right button for selecting a desired operating mode. And further, the cost and design concerns associated with additional buttons may be saved with the current invention.

Instead of buttons any other sensors maybe used like capacitive, optical or acoustic sensors, for example, and accordingly a component that detects a user input may be an identified location or contact rather than a button. The device of the invention may further provide different functions, like operation at different time periods, different light intensities or different wavelengths, for example.

A light flash as created in the second operating mode may be performed at an increased light intensity relative to the light intensity applied in the first operating mode. Further, it is possible to operate the light output at similar time periods in the second operating mode and the first operating mode, but at different light intensities, for example. There may be further functions for operating the light output, like different light frequencies, for example. Different functions may also be used in any suitable combination.

Figure 5:
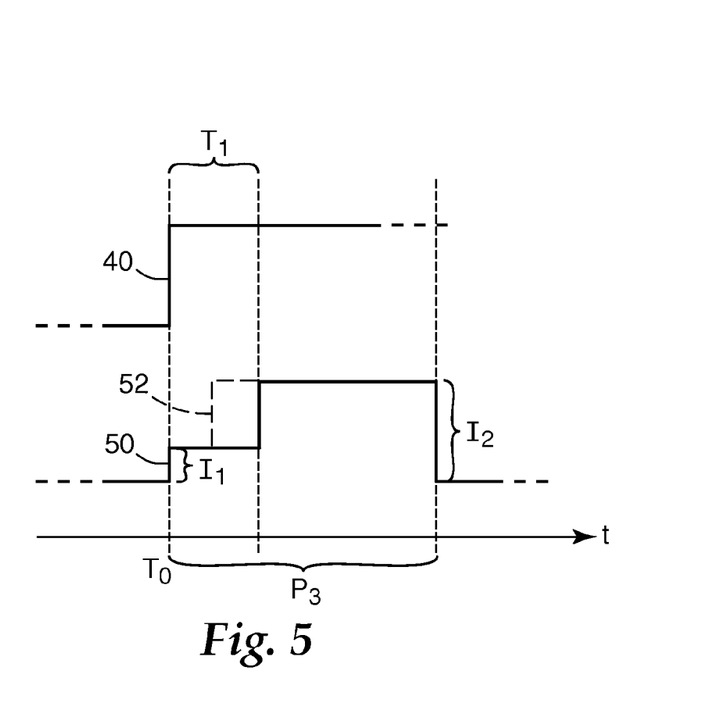
FIG. 5 is a diagram showing another alternative second operating mode of the device according to an embodiment of the invention.
Figure 6:
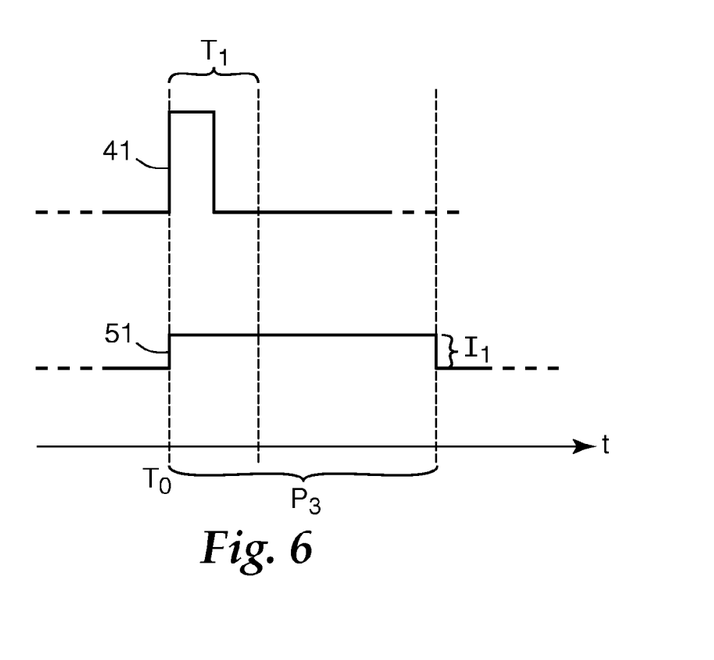
FIG. 6 is a diagram showing an alternative first operating mode of the device according to an embodiment of the invention.

FIGS. 5 and 6 show an example in which the light output is operated at different light intensity levels.

FIG. 5 shows a curve 40 which represents a relatively long actuation time period of the activator. In particular the actuation time period is longer than the monitoring time period $T_1$. This means that within the monitoring time period $T_1$ (started by a first user input) no second user input is detected.

In response, a second operating mode is activated (curve 50) in which the light output of the device is operated at a light intensity $I_1$ for the monitoring time period $T_1$, and changed to a light intensity $I_2$ after the monitoring time period has lapsed. The second operating mode automatically runs for the operating time period $P_3$ which may be pre-selected by the user. The light intensity $I_1$ and/or $I_2$ may also be pre-selected by the user, for example by help of separate buttons on the device.

In FIG. 6 the actuating time period (curve 41) is shorter than the monitoring time period $T_1$. This means that a second user input is detected within the monitoring time period, and the monitoring time period is started by a first user input. In response a first operating mode is activated in which the light output is operated at light intensity $I_1$ over the entire operating time period $P_3$.

In this example the light intensity during the monitoring time period is generally equal in the first and the second operating modes. Because the monitoring time period $T_1$ is used to determine the mode in which the device operates the light intensity may only be changed from $I_1$ to $I_2$, as shown in FIG. 5, after the monitoring time period $T_1$ has lapsed. Alternatively the change from light intensity $I_1$ to $I_2$ may be triggered by the second user input as indicated by curve 52. The intensity $I_1$ in the example is lower than the intensity $I_2$. Therefore the second operating mode 51 may be used to cure dental material applied at sensitive areas of a patients tooth. In the first operating mode (FIG. 6) the light output may also be operated at a shorter time than the time period $P_3$.

In a variant of the example shown in FIG. 5 the light output may be initially operated at the higher light intensity $I_2$ for the monitoring time period $T_1$ only, and at the lower intensity $I_1$ after. Consequently, in the first operating mode (FIG. 6) the light output may also be initially operated at the higher light intensity $I_2$, and maintained at this intensity level for the time period $P_3$ or deactivated before, for example at the end of the monitoring time $T_1$. Such a two step curing mode may provide for instantly pre-curing a dental material and smoothly ready-curing in a continuous procedure.

Figure 7:
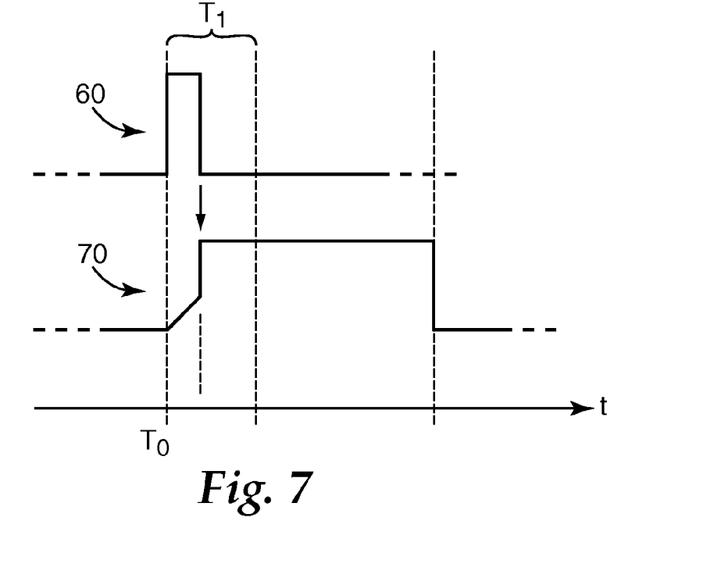
FIG. 7 is a diagram showing a further alternative first operating mode of the device according to an embodiment of the invention.
Figure 8:
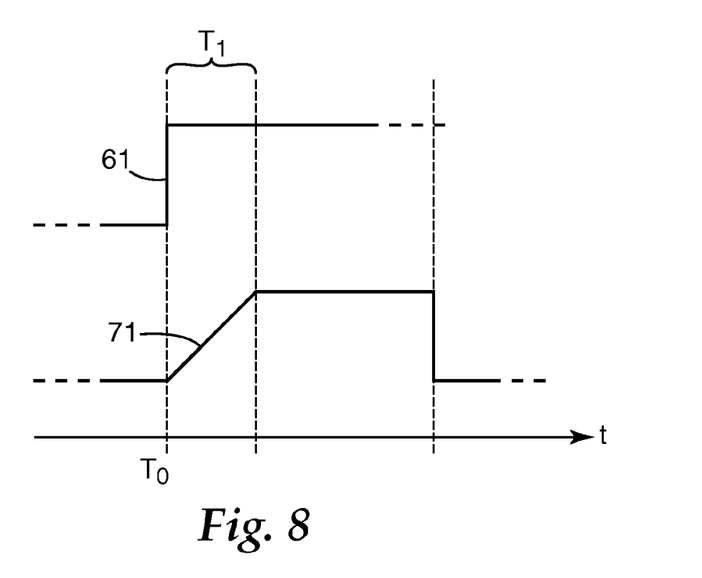
FIG. 8 is a diagram showing a further second operating mode of the device according to an embodiment of the invention.

FIGS. 7 and 8 show an alternative use of the two operating modes of the device in which a first operating mode (FIG. 7) comprises a ramp-up phase in which the light intensity of the light output is continuously increased (curve 70) after the device has been activated at the time $T_0$ by a first user input (curve 60). As soon as the second user input occurs the ramp-up phase is terminated and the light output is operated at full light intensity (for example at a pre-selected generally constant light intensity). In a second operating mode shown in FIG. 8 the ramp-up phase is not terminated (curve 71) in response to the activator maintained actuated longer than the monitoring time $T_1$ (curve 61). Thus, the full light intensity is only reached when the monitoring time period $T_1$ has lapsed. Therefore a user shortly pushing and releasing the activator button of the device may instantly activate the device at full light intensity. Or the user may smoothly increase the light intensity by holding the button down until the full light intensity has been reached. Thereby the curing speed of the dental material may be controlled at the beginning, for example to avoid irregular shrinkage and stress in the cured material.

The invention claimed is:

1. A light-emitting device comprising a switch and a light output adapted to emit light of a wavelength capable of curing a dental material, the light-emitting device being adapted to operate the light output in a first operating mode having a monitoring time period and a second operating mode, wherein the light-emitting device is adapted to operate the light output in:
   (i) the first operating mode and not the second operating mode, if the switch is activated during the monitoring time period and subsequently not activated at the end of the monitoring time period, and
   (ii) the first operating mode and the second operating mode, if the switch is activated during and through the end of the monitoring time period,
   wherein both the first and second operating modes emit the light of a wavelength and an intensity that cures the dental material.

2. The light-emitting device of claim 1, wherein the switch comprises a button, activating the switch comprises pressing the button, and not activating the switch comprises releasing the button.

3. The light-emitting device of claim 1, wherein in the first operating mode the light has a first intensity and in the second operating mode the light has a second intensity, and wherein the first intensity is less than the second intensity.

4. The light-emitting device of claim 1, wherein the wavelength is between 400 nm and 500 nm.

5. The light-emitting device of claim 1, wherein in the first operating mode the light output is activated for a first operating time period and in the second operating mode the light output is activated for a second operating time period, and wherein the first operating time period is longer than the second operating time period.

6. The light-emitting device of claim 5, wherein the first operating time period is pre-selectable by a user.

7. The light-emitting device of claim 5, wherein the first operating time period is one of about 5 seconds, about 10 seconds, about 15 seconds, and about 20 seconds.

8. The light-emitting device of claim 5, comprising another switch allowing for pre-selection of the first operating time period.

9. The light-emitting device of claim 5, wherein the second operating time period is a predetermined time period of between 0.1 seconds and 5 seconds.

10. The light-emitting device of claim 1, further comprising an on/off switch for switching the light-emitting device into a non-operative mode during the period in which the light-emitting device is operating in the first or the second operating mode.

11. The light-emitting device of claim 1, comprising a controller adapted to interpret the activation of the switch within the monitoring time period to operate the light output according to the first or the second operating mode.

12. The light-emitting device of claim 11 wherein the controller is user programmable and enables a user to determine the monitoring time period.

13. The light-emitting device of claim 1, comprising a user interface adapted to indicate the operating mode at which the light-emitting device is operating.

14. The light-emitting device of claim 13, wherein the operating mode is indicated by at least one sound.

15. A method of curing a dental material using a light-emitting device that can be operated in a first operating mode and a second operating mode, the method comprising:
   (a) providing an input on a switch of the light-emitting device; and
   (b) operating a light output of the light-emitting device in:
      (i) the first operating mode and not the second operating mode, if the switch is activated during the monitoring time period and subsequently not activated at the end of the monitoring time period; and (ii) the first operating mode and the second operating mode, if the switch is activated during and through the end of the monitoring time period, wherein in both the first and second operating modes the light output emits light of a wavelength and an intensity that cures the dental material.

16. The method of claim 15, wherein in the first operating mode the light output is activated for a first time period and in the second operating mode the light output is activated for a second time period, and wherein the second time period is shorter than the first time period.

17. The method of claim 16, wherein the first time period is between 5 seconds to 20 seconds.

18. The method of claim 16, wherein the second time period is between 0.1 seconds to 5 seconds.

19. The method of claim 15, wherein in the first operating mode the light has a first intensity and in the second operating mode the light has a second intensity, and wherein the first intensity is less than the second intensity.

* * * * *